(12) United States Patent
Opland

(10) Patent No.: US 9,878,098 B1
(45) Date of Patent: Jan. 30, 2018

(54) VIAL HOLDER

(71) Applicant: Brett Opland, Sioux Falls, SD (US)

(72) Inventor: Brett Opland, Sioux Falls, SD (US)

( * ) Notice: Subject to any disclaimer, the term of this patent is extended or adjusted under 35 U.S.C. 154(b) by 0 days.

(21) Appl. No.: 15/231,934

(22) Filed: Aug. 9, 2016

(51) Int. Cl.
*A47G 23/02* (2006.01)
*A61M 5/178* (2006.01)
*A61J 1/16* (2006.01)
*A61J 1/20* (2006.01)

(52) U.S. Cl.
CPC .............. *A61M 5/1782* (2013.01); *A61J 1/16* (2013.01); *A61J 1/201* (2015.05); *A61J 1/2096* (2013.01)

(58) Field of Classification Search
USPC ........................................................ 248/146
See application file for complete search history.

(56) References Cited

U.S. PATENT DOCUMENTS

| | | | | |
|---|---|---|---|---|
| 2,007,574 A * | 7/1935 | Lang | .............. | G10G 5/00 248/167 |
| 2,046,864 A * | 7/1936 | Baker | .............. | B01L 9/00 211/74 |
| D147,771 S * | 10/1947 | Wallack | .............. | D6/524 |
| 2,469,859 A * | 5/1949 | Charbeneau | .......... | A61J 9/0684 248/106 |
| 2,677,372 A * | 5/1954 | Barnish, Jr. | ............ | A61J 1/16 248/311.3 |
| 3,602,272 A * | 8/1971 | Stawski | ............. | A61M 5/1782 141/27 |
| 3,853,158 A * | 12/1974 | Whitty | ............. | A61J 1/2096 141/233 |
| 4,278,225 A * | 7/1981 | Phelps | ............. | A61J 1/06 248/311.3 |
| 4,377,268 A * | 3/1983 | Wolford | ............. | G10G 5/00 248/121 |
| 5,115,816 A * | 5/1992 | Lee | ............. | A61B 10/0283 600/562 |
| 5,288,285 A * | 2/1994 | Carter | ............. | A61M 5/1782 600/4 |
| 5,704,495 A * | 1/1998 | Bale | ............. | A61B 50/20 211/71.01 |
| 5,873,859 A * | 2/1999 | Muntz | ............. | A61J 1/2096 141/27 |
| 5,924,659 A | 7/1999 | Babcock | | |
| 5,975,470 A | 11/1999 | Casey | | |
| D622,377 S * | 8/2010 | Jackson | ............. | D24/128 |
| 8,967,572 B1 | 3/2015 | Glammeier | | |
| 2002/0124905 A1 | 9/2002 | Draghn | | |
| 2004/0144903 A1* | 7/2004 | Cherubini | ............. | A61J 1/16 248/231.71 |
| 2005/0167999 A1 | 8/2005 | Beal | | |

FOREIGN PATENT DOCUMENTS

WO    2011062382 A2    5/2011

* cited by examiner

*Primary Examiner* — Monica Millner

(57) ABSTRACT

The vial holder is a device that is used to support a vial or injectable bottle in a partially inverted position so as to enable a hypodermic needle of a syringe to be inserted without fear of an unintended prick to an end user. The vial holder is further defined with a weighted base that is adapted to lie on a support surface. The weighted base includes a vertical member that rises vertically. A pair of holding armatures extend upwardly and away from the vertical member. The pair of holding armatures radiate away from one another and form "V". The pair of holding armatures is adapted to support the injectable bottle at a partially inverted position.

2 Claims, 5 Drawing Sheets

VIAL HOLDER

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of vessels, more specifically, a device that holds vials.

SUMMARY OF INVENTION

The vial holder is a device that is used to support a vial or injectable bottle in a partially inverted position so as to enable a hypodermic needle of a syringe to be inserted without fear of an unintended prick to an end user. The vial holder is further defined with a weighted base that is adapted to lie on a support surface. The weighted base includes a vertical member that rises vertically. A pair of holding armatures extend upwardly and away from the vertical member. The pair of holding armatures radiate away from one another and form "V". The pair of holding armatures is adapted to support the injectable bottle at a partially inverted position.

These together with additional objects, features and advantages of the vial holder will be readily apparent to those of ordinary skill in the art upon reading the following detailed description of the presently preferred, but nonetheless illustrative, embodiments when taken in conjunction with the accompanying drawings.

In this respect, before explaining the current embodiments of the vial holder in detail, it is to be understood that the vial holder is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the vial holder.

It is therefore important that the claims be regarded as including such equivalent construction insofar as they do not depart from the spirit and scope of the vial holder. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

Figure 1:
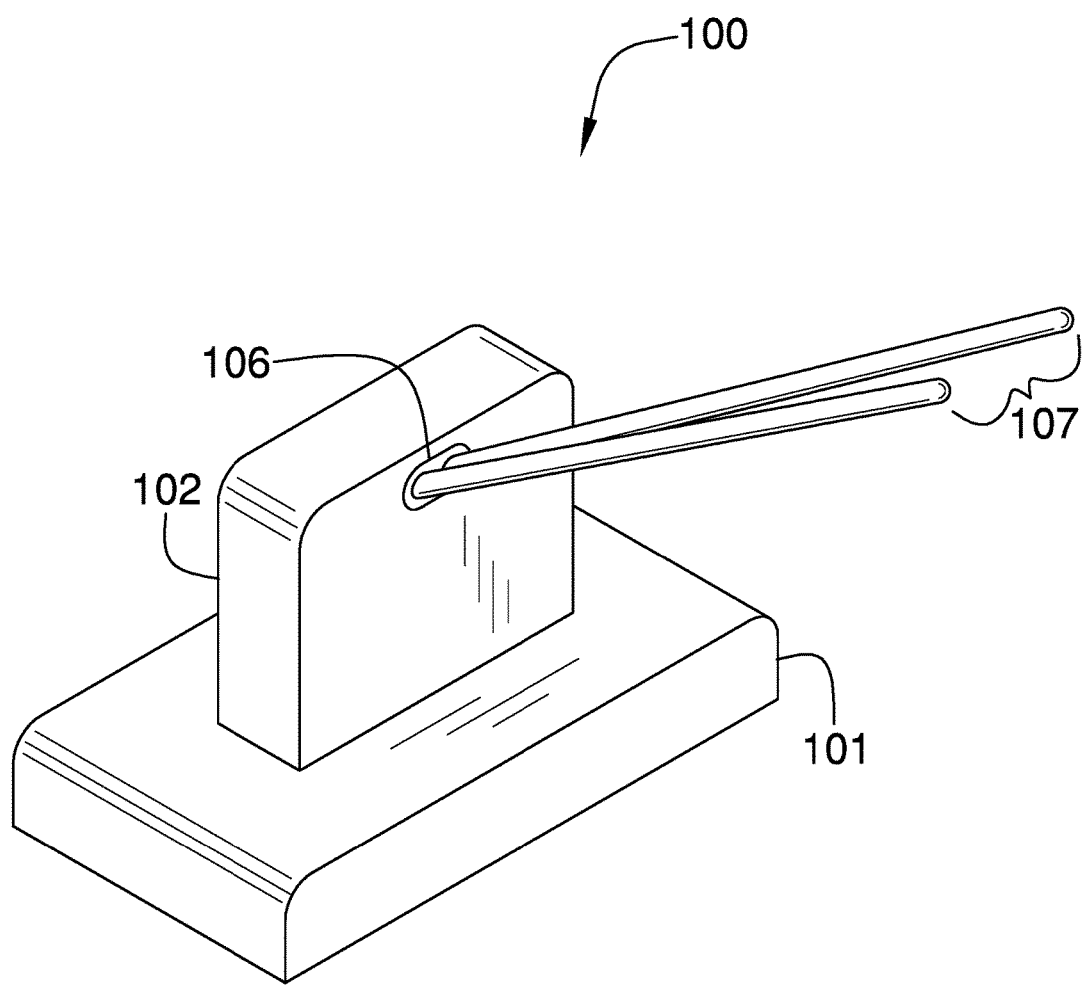
FIG. 1 is a perspective view of an embodiment of the disclosure.

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Detailed reference will now be made to one or more potential embodiments of the disclosure, which are illustrated in FIGS. 1 through 5.

The vial holder 100 (hereinafter invention) comprises a weighted base 101 that is adapted to lie on a support surface 200. The weighted base 101 is attached to a vertical member 102. The vertical member 102 extends upwardly from the weighted base 101. The vertical member 102 is further defined with a front surface 103 and a top surface 104. Located on the front surface 103 and adjacent to a top edge 105 of the vertical member 102 is a rubber insert 106 from which a pair of holding armatures 107 extend.

The vertical member 102 includes armature holes 108 that extend from the front surface 103 to a rear surface 109 of the vertical member 102. The armature holes 108 are diagonally-oriented with respect to the vertical member 102. Moreover, the rubber insert 106 is inserted into the armature holes 108. The pair of holding armatures 107 are able to slide in and out of the rubber insert 106. The pair of holding armatures 107 is further defined with a rod 110 that is partially covered in an outer sleeve 111. The rod 110 may be made of a material comprising a ceramic, wood, plastic, metal, carbon fiber composite. The outer sleeve 111 may be made of a material comprising a rubber or plastic.

The rubber insert 106 has an insert hole 112 that enables the rod 110 portion of the pair of holding armatures 107 to slide therein. The rubber insert 106 is ideally made of a rubber, but may be made of other materials comprising plastic, metal, wood, ceramic, carbon fiber composite. The pair of holding armatures 107 is selectively inserted into and removed from the rubber insert 106 as needed. The pair of holding armatures 107 is adapted to support a vial 300 at a partially inverted position.

Figure 2:
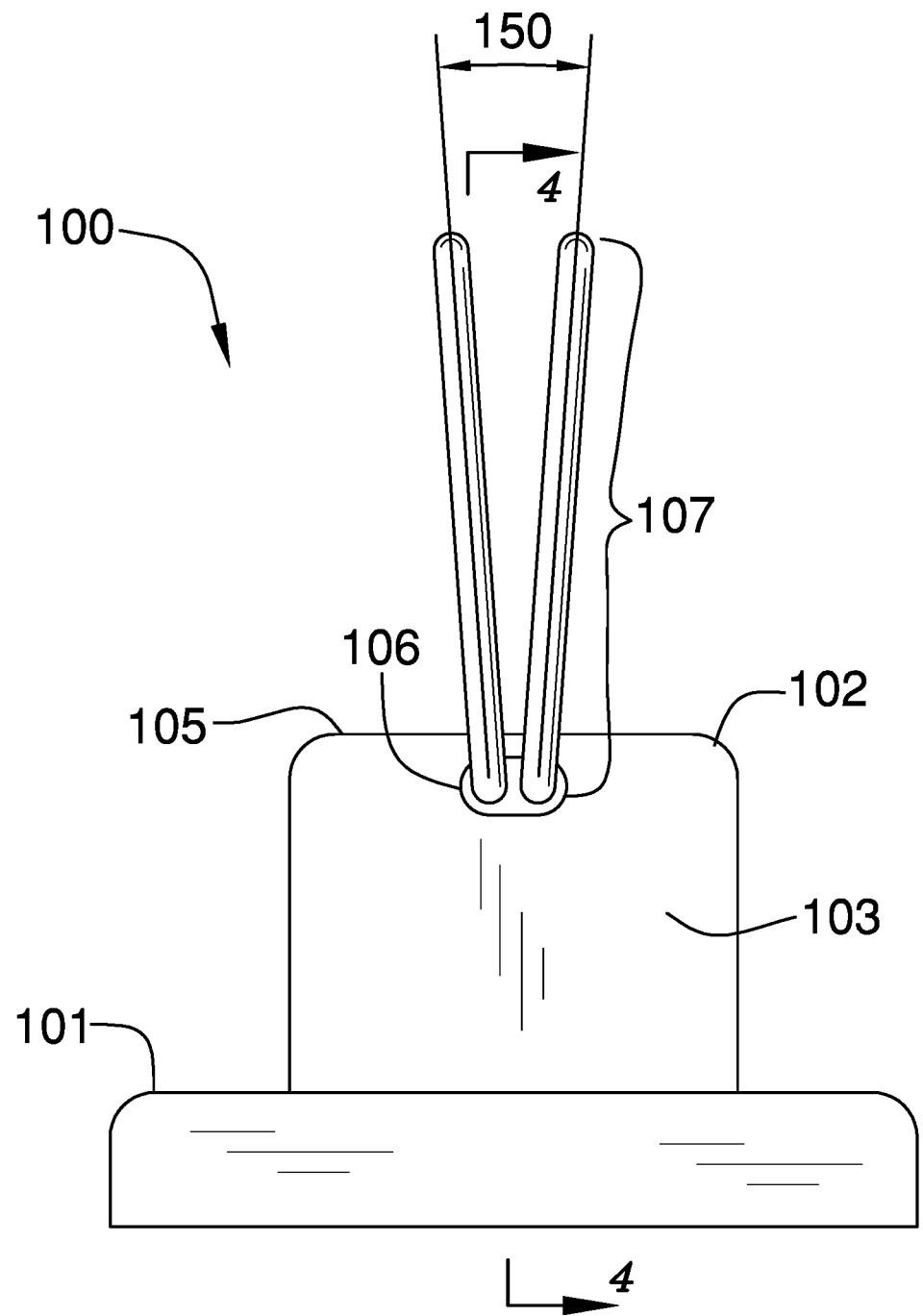
FIG. 2 is a front view of an embodiment of the disclosure.
Figure 3:
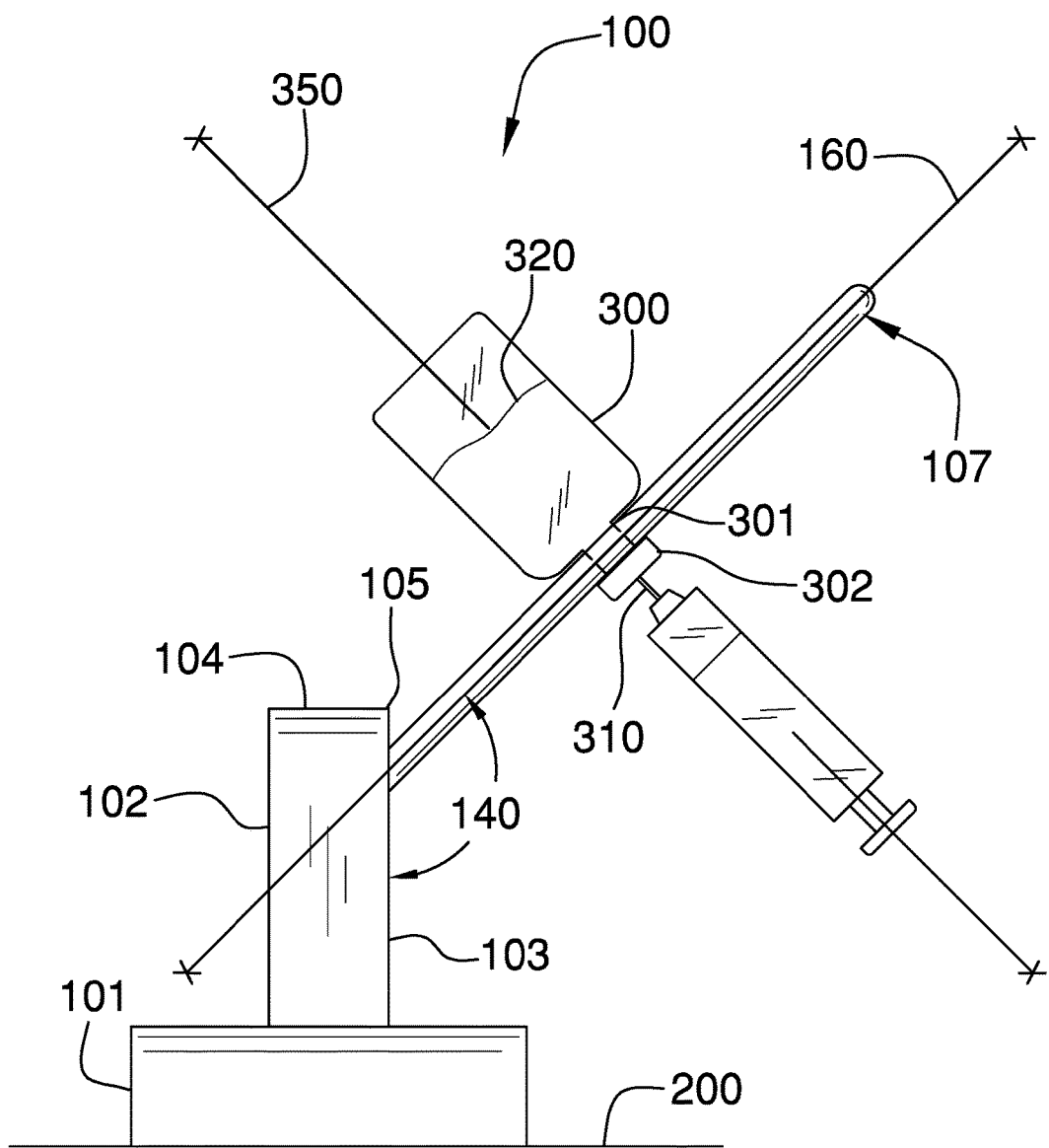
FIG. 3 is a side view of an embodiment of the disclosure in use.
Figure 4:
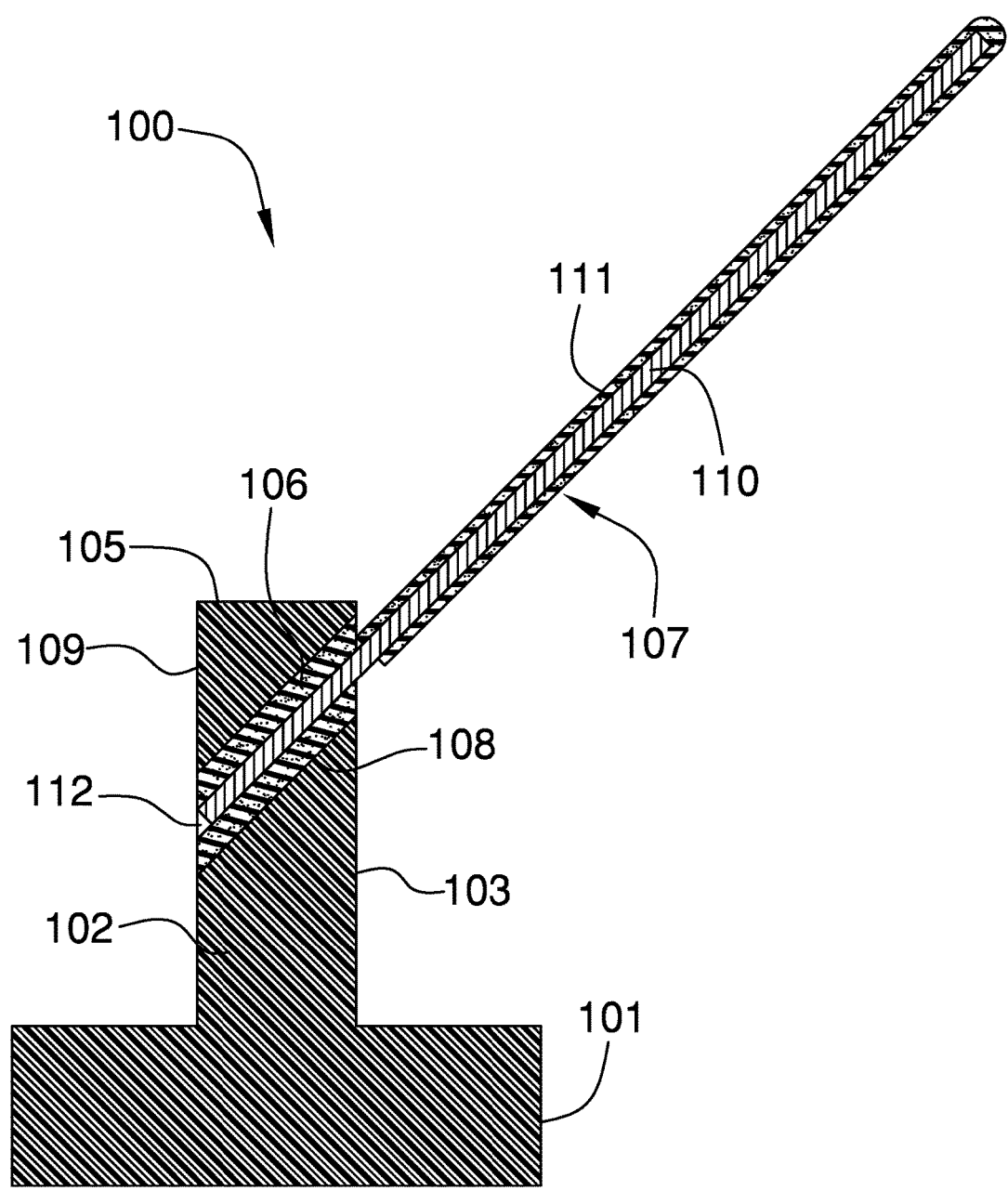
FIG. 4 is a cross-sectional view of an embodiment of the disclosure across 4-4 as shown in FIG. 2.

The pair of holding armatures 107 rest with respect to the vertical member 102 at a diagonal angle 140. The pair of holding armatures 107 forms an armature angle 150 between one another (see FIG. 2). The armature angle 150 provides that the pair of holding armatures 107 is not parallel, but slightly extend away from one another. Referring to FIG. 3, it shall be noted that the pair of holding armatures 107 are linearly aligned with respect to one another along a diagonal axis 160. FIG. 3 gives the appearance that the pair of holding armatures 107 is parallel, but FIG. 2 shows the pair of holding armatures 107 extending away from one another via the armature angle 150.

Referring to FIG. 3, the vial 300 is held at a partially inverted position via the invention 100. The vial 300 may also be referred to as an injectable bottle 300, which is well known in the art. The injectable bottle 300 is further defined with a neck 301, a top 302. The top 302 includes a diaphragm that a needle 310 can be inserted through into retrieve a solution 320 stored within the injectable bottle 300. The pair of holding armatures 107 enables the invention 100 to hold the injectable bottle 300 at a partially inverted angle via the interface of the pair of holding armatures 107 and the neck 301 of the injectable bottle 300.

To secure the injectable bottle 300 to the invention 100, a user would simply partially invert the injectable bottle 300, and slide the injectable bottle 300 down and in between the pair of holding armatures 107. More specifically, the pair of holding armatures 107 enable the neck 301 of the injectable bottle 300 to be aligned in between and slid down the pair of holding armatures 107 until the injectable bottle 300 comes to rest. Since the pair of holding armatures 107 form the armature angle 150, the neck 301 of the injectable bottle 300 will come to form a snug grip amongst the pair of holding armatures 107. It shall be noted that once the injectable bottle 300 comes to rest on the pair of holding armatures 107, the injectable bottle 300 is supported at a partially inverted axis 350. The partially inverted axis 350 is perpendicular with respect to the diagonal axis 160 of the pair of holding armatures 107.

Figure 5:
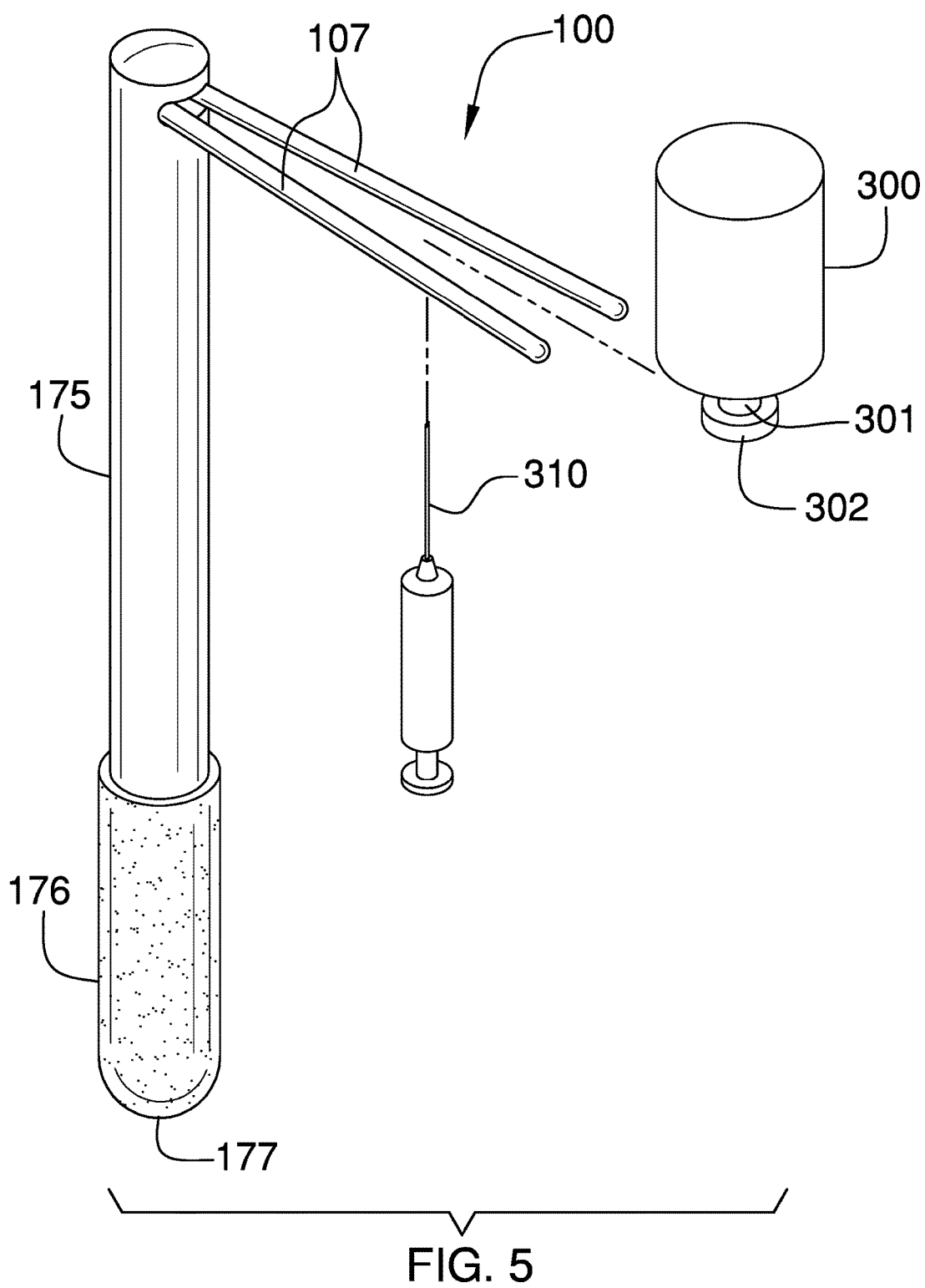
FIG. 5 is a perspective view of an alternative embodiment of the disclosure.

Referring to FIG. 5, the invention 100 may include an alternative embodiment that is manually used. The base 101 and the vertical member 102 are exchanged for a vertical armature 175. The vertical armature 175 includes the pair of holding armatures 107. Moreover, the vertical armature 175 includes a handle 176 on a bottom distal end 177 of the vertical armature 175. The pair of holding armatures 107 is distal from the bottom distal end 177. The pair of holding armatures 107 may be permanently affixed to the vertical armature 175 or utilize a rubber insert to provide temporary support.

To use the invention 100 of FIG. 5, a user would simply grasp the handle 176 to support the injectable bottle 300 at a partially inverted or wholly inverted position while inserting the needle 310 through the diaphragm of the top 302 of the injectable bottle 300.

With respect to the above description, it is to be realized that the optimum dimensional relationship for the various components of the invention described above and in FIGS. 1 through 5, include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:

1. A safety device comprising:
    a vial holder that is adapted to support an injectable bottle at a partially inverted position so as to inject a needle into said injectable bottle in order to extract a solution from said injectable bottle;
    wherein the vial holder supports the injectable bottle in order to eliminate unintended pricking of said needle with an end user thereby creating a safety enhancement with respect to needles and injectable bottles;
    wherein the vial holder is manually supported;
    wherein a vertical armature is attached to a pair of holding armatures;
    wherein the vertical armature includes a handle on a bottom distal end of the vertical armature;
    wherein the pair of holding armatures is distal from the bottom distal end;
    wherein the pair of holding armatures is further defined with a rod that is partially covered in an outer sleeve;
    wherein the pair of holding armatures is adapted to support the injectable bottle at the partially inverted or wholly inverted position;
    wherein the pair of holding armatures forms an armature angle between one another;
    wherein the armature angle makes the pair of holding armatures at a not parallel arrangement;
    wherein the pair of holding armatures extend away from one another.

2. The safety device according to claim 1 wherein the pair of holding armatures are linearly aligned with respect to one another along a diagonal axis; wherein the pair of holding armatures holds the injectable bottle at a partially inverted angle via the interface of the pair of holding armatures and a neck of the injectable bottle; wherein the pair of holding armatures enables the neck of the injectable bottle to be aligned in between and slid down the pair of holding armatures until the injectable bottle comes to rest; wherein since the pair of holding armatures form the armature angle, the neck of the injectable bottle forms a snug grip amongst the pair of holding armatures.

\* \* \* \* \*